United States Patent
Kaneko et al.

(10) Patent No.: US 10,878,560 B2
(45) Date of Patent: Dec. 29, 2020

(54) RADIATION IMAGE PROCESSING APPARATUS AND RADIATION IMAGE CAPTURING SYSTEM

(71) Applicant: Konica Minolta, Inc., Tokyo (JP)

(72) Inventors: Shikou Kaneko, Niiza (JP); Keiko Itaya, Hino (JP); Shinsuke Katsuhara, Kodaira (JP)

(73) Assignee: KONICA MINOLTA, INC., Tokyo (JP)

(*) Notice: Subject to any disclaimer, the term of this patent is extended or adjusted under 35 U.S.C. 154(b) by 246 days.

(21) Appl. No.: 15/926,328

(22) Filed: Mar. 20, 2018

(65) Prior Publication Data
US 2018/0276816 A1 Sep. 27, 2018

(30) Foreign Application Priority Data

Mar. 23, 2017 (JP) ................. 2017-056991

(51) Int. Cl.
*G06T 7/00* (2017.01)
*A61B 6/00* (2006.01)
*A61B 6/03* (2006.01)

(52) U.S. Cl.
CPC ............ *G06T 7/0012* (2013.01); *A61B 6/03* (2013.01); *A61B 6/032* (2013.01); *A61B 6/463* (2013.01); *A61B 6/464* (2013.01); *A61B 6/486* (2013.01); *A61B 6/50* (2013.01); *A61B 6/503* (2013.01); *A61B 6/504* (2013.01); *A61B 6/507* (2013.01);

(Continued)

(58) Field of Classification Search
CPC ................ A61B 6/463; A61B 6/486
See application file for complete search history.

(56) References Cited

U.S. PATENT DOCUMENTS

2006/0064396 A1* 3/2006 Wei ..................... A61B 6/5235
2008/0075227 A1* 3/2008 Christoph ............ A61B 6/584
378/23

(Continued)

FOREIGN PATENT DOCUMENTS

| JP | 2012110397 A | 6/2012 |
| JP | 2012110466 A | 6/2012 |
| WO | 2014/192504 A1 | 12/2014 |

OTHER PUBLICATIONS

Japanese Patent Office, Office Action dated Jul. 21, 2020 issued in connection with corresponding Japanese Patent Application No. 2017-056991 and English machine translation (5 pages).

*Primary Examiner* — Gandhi Thirugnanam
(74) *Attorney, Agent, or Firm* — Lucas & Mercanti, LLP

(57) ABSTRACT

A radiation image processing apparatus includes a display and a hardware processor. The display displays an image. The hardware processor is configured to perform the following, acquire radiographic moving image data comprising a plurality of frame images, subject the moving image data to predetermined analytical processing, generate an analyzed moving image comprising a plurality of analyzed frame images, select a plurality of specific analyzed frame images from the analyzed frame images of the analyzed moving image, derive a calculation signal value based on signal values of pixels having common coordinates positioned in common coordinates in the selected specific analyzed frame images, and cause a calculated image based on the calculation signal values generated according to coordinates to appear on the display.

9 Claims, 14 Drawing Sheets

(52) U.S. Cl.
CPC .......... *A61B 6/5205* (2013.01); *A61B 6/5217* (2013.01); *A61B 6/5223* (2013.01)

(56) References Cited

U.S. PATENT DOCUMENTS

| | | | | |
|---|---|---|---|---|
| 2012/0130238 | A1* | 5/2012 | Muraoka | A61B 6/4233 |
| | | | | 600/436 |
| 2016/0098836 | A1* | 4/2016 | Yamato | A61B 6/50 |
| | | | | 382/128 |
| 2016/0104283 | A1* | 4/2016 | Fujiwara | G06T 7/0016 |
| | | | | 382/132 |
| 2016/0120491 | A1* | 5/2016 | Shimamura | A61B 6/463 |
| | | | | 348/333.05 |
| 2016/0350923 | A1* | 12/2016 | Muraoka | G06T 7/20 |
| 2018/0276816 | A1* | 9/2018 | Kaneko | A61B 6/032 |

* cited by examiner

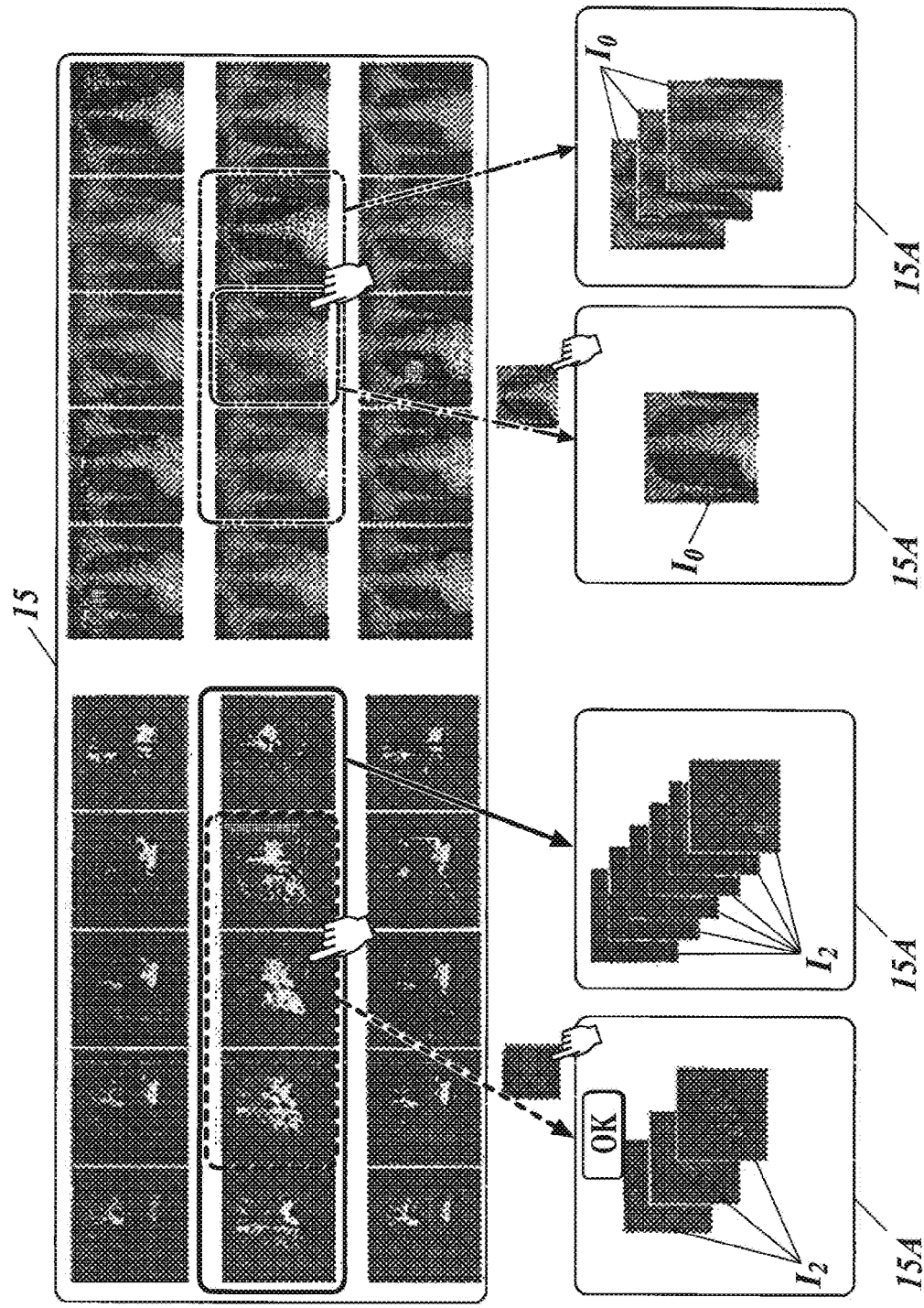

*FIG.15*
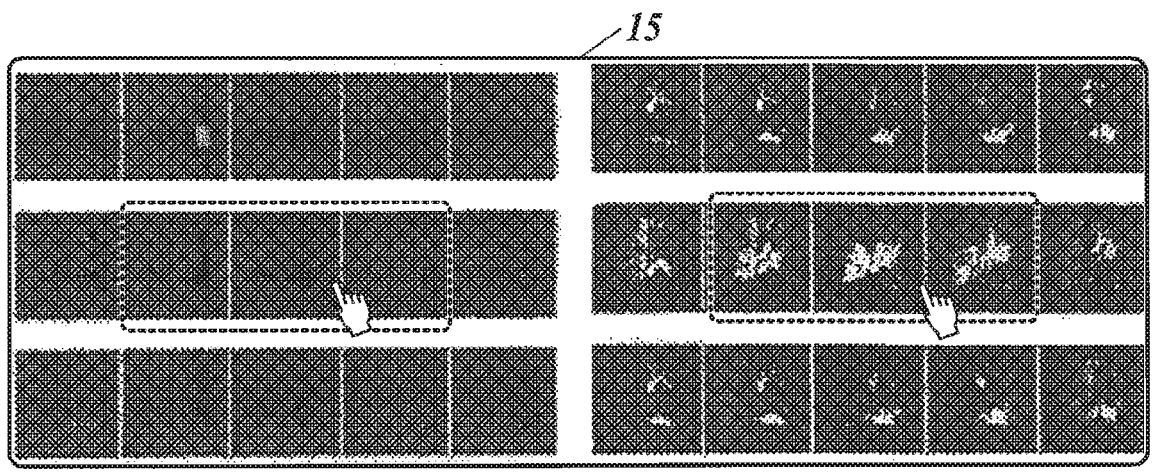
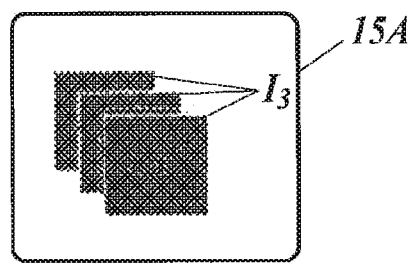
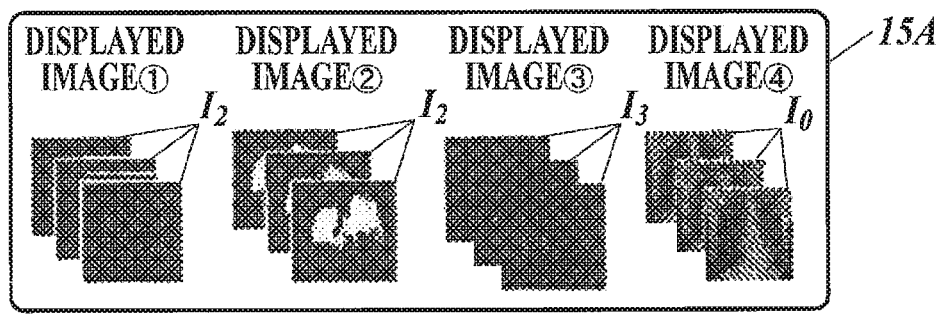
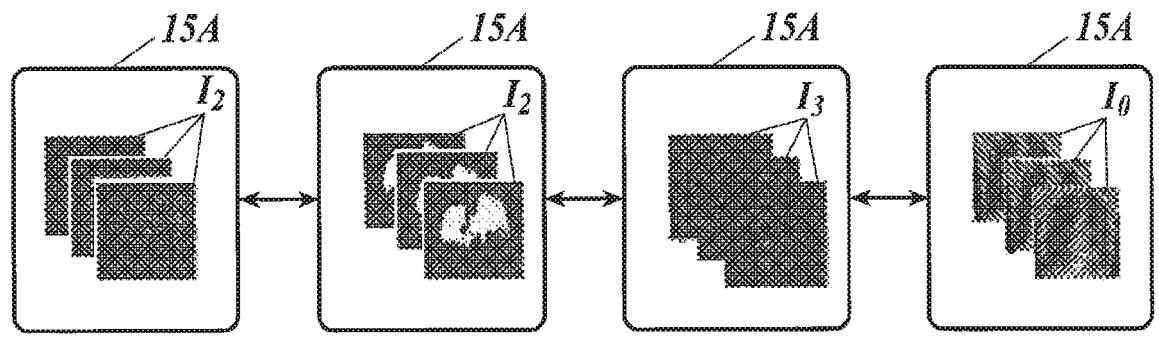

RADIATION IMAGE PROCESSING APPARATUS AND RADIATION IMAGE CAPTURING SYSTEM

CROSS-REFERENCE TO RELATED APPLICATIONS

The entire disclosure of Japanese Patent Application No. 2017-056991 filed on Mar. 23, 2017 is incorporated herein by reference in its entirety.

BACKGROUND

Technological Field

The present invention relates to a radiation image processing apparatus and a radiation image capturing system including the radiation image processing apparatus.

Description of the Related Art

Moving images captured with medical modalities (for example, computed radiography (CR) or computed tomography (CT)) are presented on displays for diagnosis by medical practitioners. The captured moving images may be displayed as they are or after various types of analytical processing.

In a known technique, a list of frame images of a moving image is displayed on a display and frame images for analysis are selected from the list (refer to Japanese Patent Application Laid-Open Publication No. 2012-110397). In another known technique, images are subjected to appropriate image processing before real-time display, reference display, or transmission (refer to Japanese Patent Application Laid-Open Publication No. 2012-110466).

In the traditional art, as is disclosed in Japanese Patent Application Laid-Open Publication No. 2012-110397 and Japanese Patent Application Laid-Open Publication No. 2012-110466, a user should visually compare an original moving image and an analyzed moving image or moving images after different types of analysis only by alternatingly shifting the view between the target regions in the moving images simultaneously displayed. Moving images are concurrently played back. In the case where the user visually determines a target region in a first moving image and intends to compare this region with the corresponding region in a second moving image, the user shifts the view to the corresponding region in the second moving image. Thus, the frame image of interest in the second moving image is already played at the time the user shifts the view and the frame image thereafter is displayed. As a result, the second moving image should be rewound to the relevant frame image before the user shifts in some cases when the user shifts the view from the first moving image to the second moving image.

In other words, interpretation or diagnosis of a moving image, which contains a large volume of information that varies over time, is difficult and inflicts an excessive burden on the user.

SUMMARY

An object of the present invention, which has been conceived in light of the drawbacks described above, is to achieve ready interpretation of target information in a moving image captured with a medical modality.

To achieve at least one of the abovementioned objects, according to an aspect of the present invention, a radiation image processing apparatus reflecting one aspect of the present invention includes a display which displays an image; and a hardware processor which is configured to, acquire radiographic moving image data comprising a plurality of frame images, subject the moving image data to predetermined analytical processing, generate an analyzed moving image comprising a plurality of analyzed frame images, select a plurality of specific analyzed frame images from the analyzed frame images of the analyzed moving image, derive a calculation signal value based on signal values of pixels having common coordinates positioned in common coordinates in the selected specific analyzed frame images, and cause a calculated image based on the calculation signal values generated according to coordinates to appear on the display.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as definition of the limits of the present invention.

FIG. 13 is a conceptual diagram illustrating image processing by a radiation image processing apparatus according to a modification of any one of the first to third embodiments.

FIG. 15 is a conceptual diagram illustrating the image processing by the radiation image processing apparatus according to the modification.

DETAILED DESCRIPTION OF EMBODIMENTS

Embodiments of the present invention will now be described in detail with reference to the accompanying drawings. The drawings should not be construed to limit the scope of the invention.

First Embodiment

[Configuration of Radiation Image Capturing System]

Figure 1:
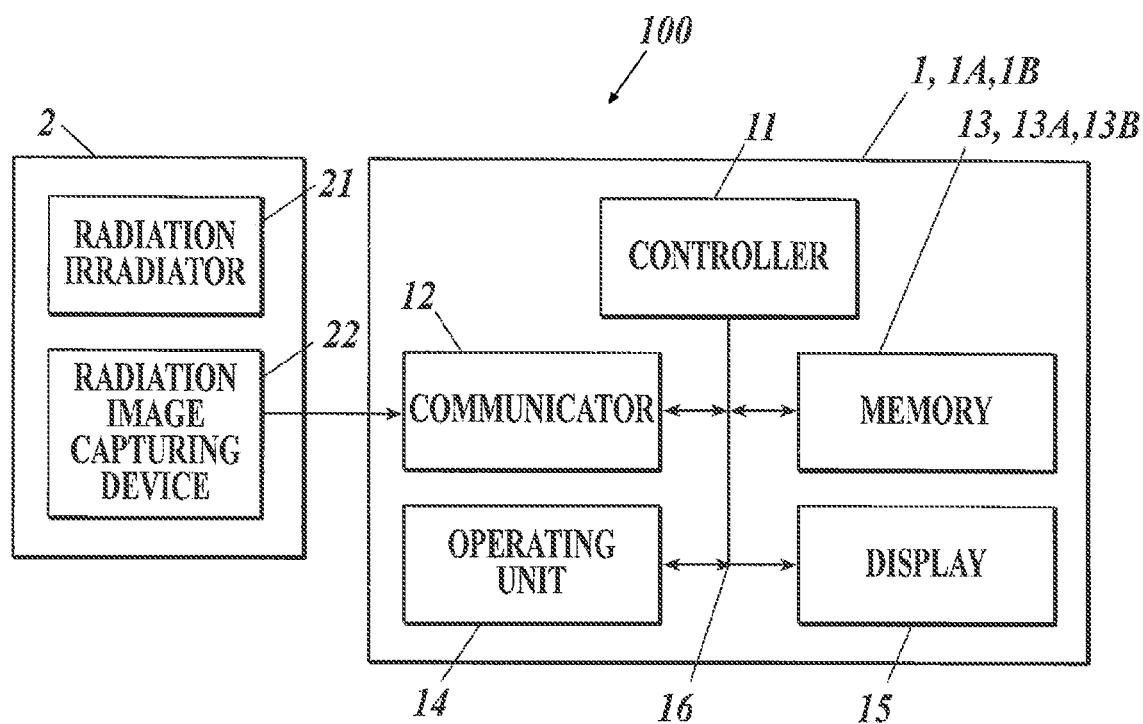
FIG. 1 is a block diagram illustrating the overall configuration of a radiation image capturing system according to any one of the first to third embodiments of the present invention.

A configuration of a radiation image capturing system 100 according to the first embodiment of the present invention will now be described. FIG. 1 is a block diagram illustrating the functional configuration of the radiation image capturing system 100 according to this embodiment.

The radiation image capturing system 100 according to this embodiment includes a radiation image processing apparatus 1 and a medical modality 2.

The radiation image capturing system 100 is connected to a console or server (for example, a picture archiving and communication system (PACS)) (not shown) as required.

The components of the radiation image capturing system 100 meet the digital image and communications in medicine (DICOM) standard and communicate with each other in accordance with the DICOM.

The modality 2 includes a radiation irradiator 21 and a radiographic-image capturing apparatus 22.

Although not illustrated, the radiation irradiator 21 includes a radiation source including a rotating anode that generates radiation and a filament that emits electron beams to the rotating anode, and a generator causing the radiation source to emit radiation in a volume corresponding to parameters, such as the tube voltage, the tube current, and the irradiation time (mAs value).

The radiation irradiating device 21 emits radiation to the radiographic-image capturing apparatus 22 in response to a user operation.

Although not illustrated, the radiographic-image capturing apparatus 22 includes a substrate provided with a two-dimensional array (matrix) of radiation detectors that accumulate charges in proportion to the intensity of incident radiation, a reading circuit that reads the charges accumulated in the radiation detectors in the form of image data, and a communication device that communicates with external units and transmits the image data.

The radiographic-image capturing apparatus 22 receives radiation from the radiation irradiator 21, reads image data, and immediately transmits the image data to an external unit via the communication device.

The modality 2 including the radiation irradiator 21 and the radiographic-image capturing apparatus 22 continuously repeats emission of radiation from the radiation irradiator 21 and accumulation of charges and reading of image data by the radiographic-image capturing apparatus 22, to generate radiographic moving image data consisting of multiple frame images.

The radiation irradiator 21 may be integrated with the radiographic-image capturing apparatus 22, such as in a CT scanner.

[Configuration of Radiation Image Capturing System]

The configuration of the radiation image processing apparatus 1 of the radiation image capturing system 100 will now be described.

With reference to FIG. 1, the radiation image processing apparatus 1 is a computer or a dedicated controller and includes a controller 11, a communicator 12, a memory 13, an operating unit 14, and a display 15. These components are connected with each other via a bus 16.

The controller 11 includes a central processing unit (CPU) and a random access memory (RAM). The CPU of the controller 11 comprehensively controls the operation of the components of the radiation image processing apparatus 1 in accordance with operation of the operating unit 14, for example, by reading system programs and various processing programs stored in the memory 13 and loading these programs to the RAM, carrying out various processing, such as the image analysis program described below, in accordance with the loaded programs, and controlling the content appearing on the display 15.

The communicator 12 includes a local area network (LAN) adapter, a modem, or a terminal adapter (TA). The communicator 12 controls the transmission and reception of data among the radiographic-image capturing apparatus 22 and other components, such as a console and a server, via a communication network NT.

The memory 13 includes a non-volatile semiconductor memory or a hard disk. The memory 13 stores programs (for example, the image analysis program and image calculation program described below) for the controller 11 to execute the various processes (for example, the image analysis process and image calculation process described below), parameters required by the programs to execute the processes, the results of the processes, and unprocessed or original moving images and still images and processed moving images and still images. The various programs are stored in the form of readable program codes.

The operating unit 14 includes a keyboard including cursor keys, numeric keys, and function keys and a pointing device, such as a mouse, operable by the user. The operating unit 14 sends instruction signals to the controller 11 in response to a key operation of the keyboard or a mouse operation.

The operating unit 14 may further include a touch panel on the display screen of the display 15. In such a case, instruction signals input via the touch panel are sent to the controller 11.

The display 15 includes a monitor, such as a liquid crystal display (LCD) or a cathode ray tube (CRT). The display 15 displays various images, instructions from the operating unit 14, and various data items in accordance with the instructions corresponding to display signals from the controller 11.

[Operation of Radiation Image Processing Apparatus]

The operation of the radiation image processing apparatus 1 according to this embodiment will now be described.

Figure 2:
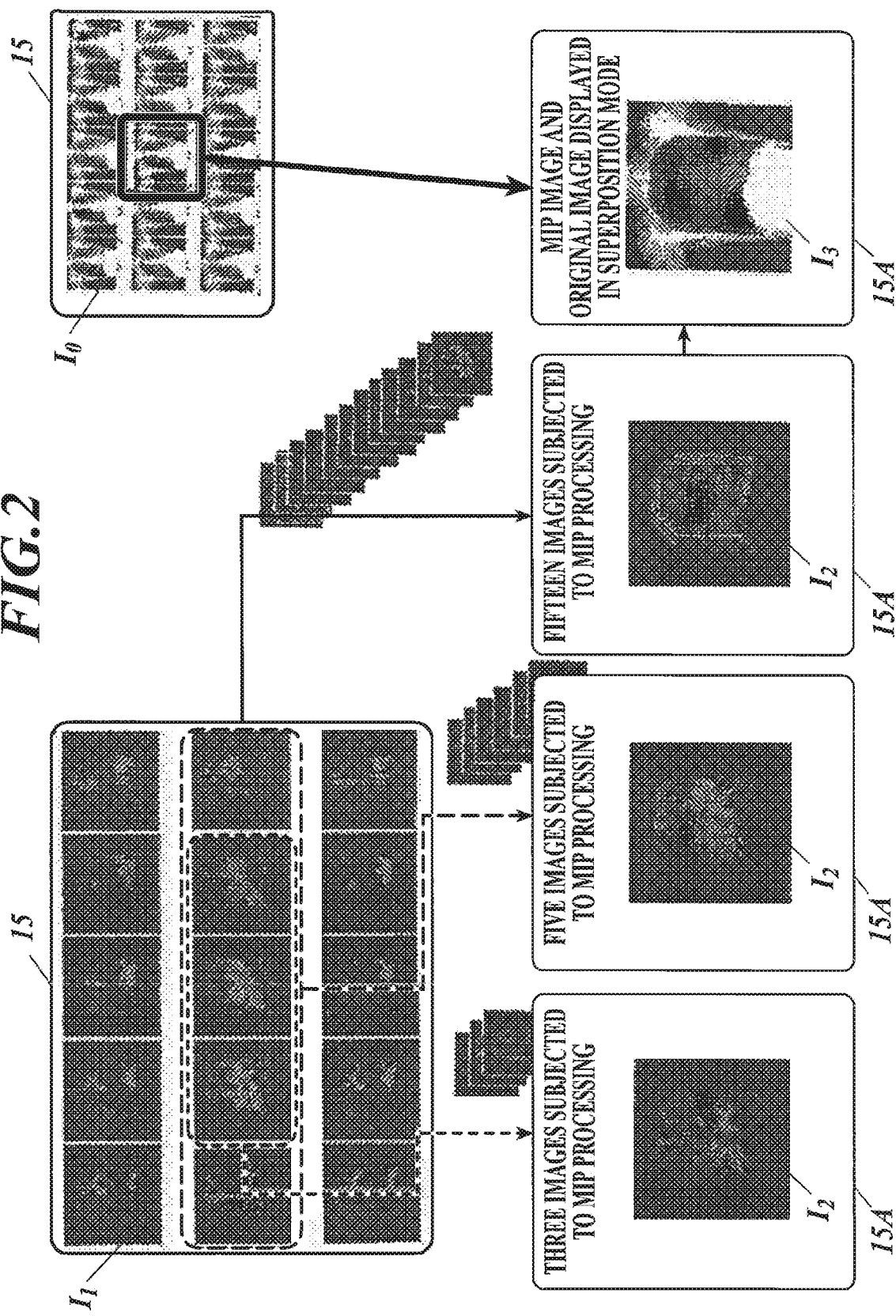
FIG. 2 is a conceptual diagram illustrating image processing by a radiation image processing apparatus according to the first embodiment.
Figure 3:
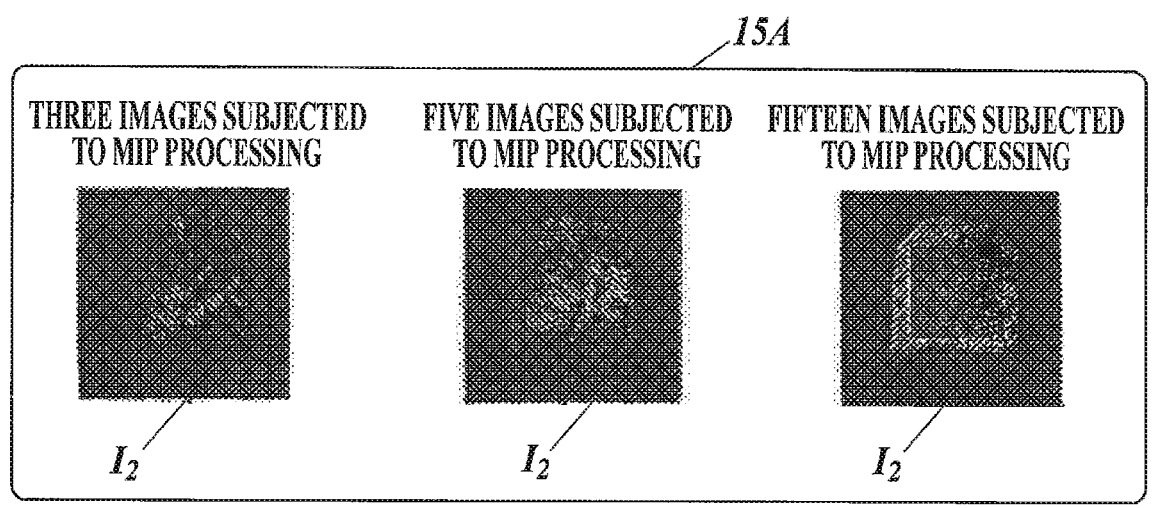
FIG. 3 illustrates example results of the image processing displayed by the radiation image processing apparatus according to the first embodiment.
Figure 4A:
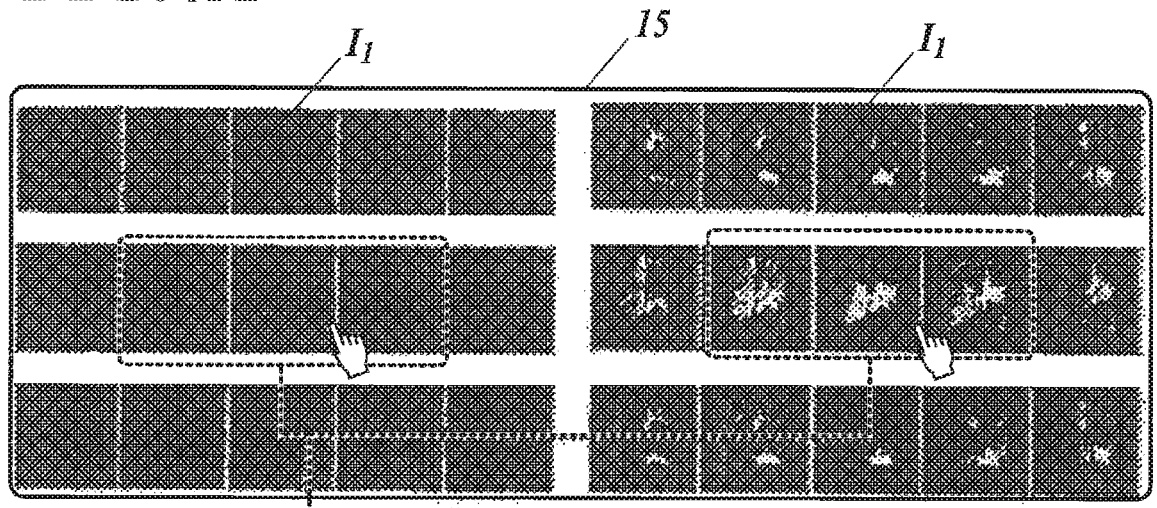
FIG. 4A is a conceptual diagram illustrating image selection by the radiation image processing apparatus according to the first embodiment.
Figure 4B:
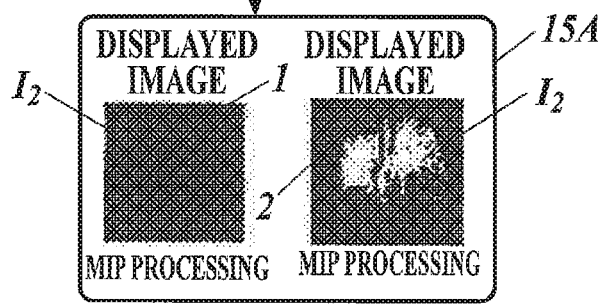
FIGS. 4B, 4C, and 4D illustrate example results of the image processing displayed by the radiation image processing apparatus according to the first embodiment.

FIGS. 2 and 4 are conceptual diagrams illustrating image processing by the radiation image processing apparatus 1. FIGS. 3 and 5 illustrate example results of the image processing.

The radiation image processing apparatus 1 according to this embodiment can process and display still images. However, processing and display of moving images will be mainly described in this embodiment. The drawings include example images of the lung field. Alternatively, the radiation image processing apparatus 1 according to this embodiment may process and display moving images of sites other than the lung field.

In response to a user instruction via the operating unit 14 for displaying an unprocessed original radiographic moving image, the controller 11 of the radiation image processing apparatus 1 acquires original moving image data, such as raw data, of a radiographic moving image consisting of multiple frame images (i.e., receives the data from the modality 2, the console, or the server via the communicator 12 or retrieves the data from the memory 13) and causes a group or list of original frame images $I_0$ of the original moving image based on the acquired original moving image data or the original moving image illustrated in FIG. 2, to appear on the display 15. In other words, the controller 11 functions as an image acquisition means according to the present invention. Although the reference sign $I_0$ in FIG. 2 indicates an original frame image, the reference sign $I_0$ in the description below indicates any image (original moving image or original frame image) appearing on the display 15 on the basis of the original moving image data.

In response to a user instruction via the operating unit 14 for dynamic analysis of the original moving image data, the controller 11 acquires original moving image data, such as raw data, analyzes the original moving image data in various ways (such as ventilation analysis and hemodynamic analysis) in cooperation with the image analysis program stored in the memory 13, and generates analyzed moving image data, which is the analytical results.

The controller 11 causes a list of analyzed frame images $I_1$ of an analyzed moving image based on the analyzed moving image data or an analyzed moving image illustrated in FIG. 2, to appear on the display 15 in response to an automatic instruction or a user instruction. In other words, the controller 11 functions as an analysis means according to the present invention. Although the reference sign $I_1$ in FIG. 2 indicates an analyzed frame image, the reference sign $I_1$ in the description below indicates any image (analyzed moving image or analyzed frame image) appearing on the display 15 on the basis of the analyzed moving image data.

In response to a user instruction via the operating unit 14 for subjecting the analyzed moving image data to calculation, the controller 11 acquires the analyzed moving image data, subjects the analyzed moving image data to various calculation processes in cooperation with the image calculation program stored in the memory 13, and generates calculated image data, which is the results of the calculation processes.

Alternatively, the original moving image data may be subjected to calculation to generate calculated image data.

The calculation starts in response to selection of analyzed frame images $I_1$ (all or some of the analyzed frame images $I_1$ of the analyzed moving image) in the list of analyzed frame images $I_1$ of the analyzed moving image appearing on the display 15. Hereinafter, the selected analyzed frame images $I_1$ are referred to as specific analyzed frame images $I_1$.

Figure 17:
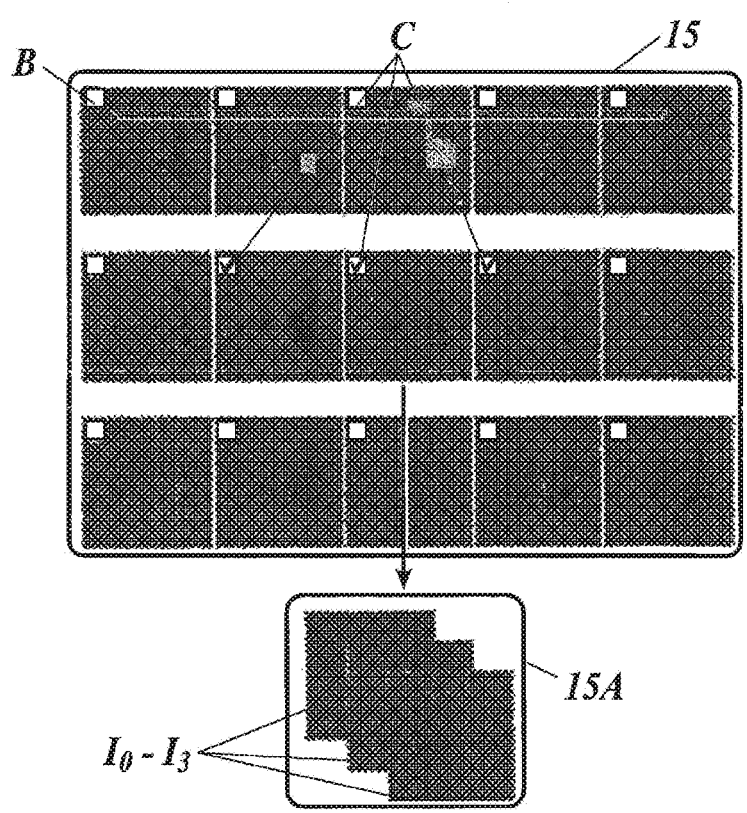
FIG. 17 is a conceptual diagram illustrating the image processing by the radiation image processing apparatus according to the modification.

In this embodiment, the specific analyzed frame images $I_1$ are selected in accordance with a user operation via the operating unit 14. In detail, the specific analyzed frame images $I_1$ are selected, for example, from the list of the analyzed frame images $I_1$ of the analyzed moving image appearing on the display 15, as illustrated in FIG. 2, by dragging or dropping the specific analyzed frame images $I_1$ selected as targets of processing by the user to a predetermined region, such as the summary display region described below, or placing checks C in checkboxes B disposed near the edges of the analyzed frame images $I_1$, as illustrated in FIG. 17. In other words, the controller 11 functions as a selection means according to the present invention.

The selected analyzed frame images $I_1$ do not necessarily have to be consecutive frame images; every several analyzed frame images $I_1$ may be selected.

In the calculation process, a calculation signal value is derived from signal values of a group of pixels having common coordinates in the selected specific analyzed frame images $I_1$. This process is repeated for the coordinates (1,1) to (m,n), to generate calculated image data items corresponding to a calculated image $I_2$ from the calculation signal values of the respective coordinates. In other words, the controller 11 functions as a calculation means according to the present invention. Hereinafter, the pixels of the specific analyzed frame images $I_1$ having common coordinates are referred to as common coordinate pixels.

The calculation signal values may be determined through, for example, a process of determining the maximum (maximum intensity projection (MIP)), the minimum (minimum intensity projection (MinIP), the peak-to-peak (Pk-Pk) value, the standard deviation, the mode, the integral, the average, the maximum derivative, or the minimum derivative. The controller 11 derives the calculation signal values through one of these processes in response to an automatic instruction or a user instruction.

In the process of determining the maximum, the maximum signal value of common coordinate pixels in the specific analyzed frame images $I_1$ is extracted and determined as a calculation signal value. The maximum value of the analytical results (ventilation or hemodynamics) can be determined from the analyzed image acquired through this process. Thus, the presence of ventilation or blood flow can be readily determined at a glance. In specific, the level of recovery of the ventilation or hemodynamic function can be readily determined in an atelectatic or pulmonary embolic region. This can also reduce processing costs.

In the process of determining the minimum, the minimum signal value of common coordinate pixels in the specific analyzed frame images $I_1$ is extracted as a calculation signal value. The minimum value of the analytical results (ventilation or hemodynamics) can be determined from the analyzed image acquired through this process. Thus, the decrease of ventilation or hemodynamic function can be readily determined. This can also reduce processing costs.

In the process of determining the mode, the modal signal value of common coordinate pixels in the specific analyzed frame images $I_1$ is extracted as a calculation signal value. The mode of the analytical results (ventilation or hemodynamics) can be determined from the analyzed image acquired through this process. Thus, the presence of ventilation or blood flow can be determined at a glance while reducing the influence of specific noise or artifacts. For example, the mode can be determined in the analytical results corresponding to, for example, several breaths or several heartbeats, to reduce the influence of a fluctuation in the breathing or heartbeat.

In the process of determining the Pk-Pk value, the maximum and minimum signal values of common coordinate pixels in the specific analyzed frame images $I_1$ are extracted, the ratio of the maximum signal value to the minimum signal value or the difference between the maximum and minimum signal values is calculated, and the ratio of the difference between the maximum and minimum signal values to the number of specific analyzed frame images is calculated as a calculation signal value. The fluctuation in the analytical results (ventilation or hemodynamics) can be determined from the analyzed image acquired through this process. Thus, the presence of ventilation or blood flow can be determined at a glance. For example, regions of atelectasis and pulmonary embolism can be readily determined (robust results that are not readily affected by fluctuation in the signals can be determined).

In the process of determining the standard deviation, the standard deviation of the signal values of common coordinate pixels in the specific analyzed frame images $I_1$ is calculated as a calculation signal value. The fluctuation in the analytical results (ventilation or hemodynamics) can be determined from the analyzed image acquired through this process without a complicated calculation algorithm. Thus, the presence of ventilation or blood flow can be determined at a glance. For example, regions of atelectasis and pulmonary embolism can be readily determined. Processing costs can also be reduced.

In the process of determining the integral, the integral of the signal values of common coordinate pixels in the specific analyzed frame images $I_1$ is calculated as a calculation signal value. The integrated value of the analytical results (ventilation or hemodynamics) corresponding to a predetermined time period can be determined from the analyzed image acquired through this process. Thus, the influence of noise and artifacts can be reduced, and the presence of ventilation or blood flow can be readily determined at a glance. The integration of the analytical results corresponding to several breaths or heartbeats can reduce the influence of a variation in breathing or heartbeat. This process can derive an integral corresponding to a predetermined time period or a physical quantity similar to those derived from the output of another modality (for example, scintigraphy) that outputs an image as a final result. The process of integration enables a ready comparison with the information of different modalities. As a result, the accuracy of the diagnosis is enhanced. Since pixel values are correlated with intensity, the total dose of radiation or total exposure can be readily estimated for efficient exposure control of the target.

In the process of determining the average, the average of the signal values of common coordinate pixels in the specific analyzed frame images $I_1$ is calculated as a calculation signal value. The analyzed image acquired through this process can be viewed to determine the presence of ventilation or blood flow at a glance after reduction in the influence of noise or artifacts. For example, the average of the analytical results corresponding to several breaths or heartbeats can be determined to reduce the influence of a variation in the breathing or heartbeat.

In the process of determining the maximum derivative, the differences or ratios between the signal values of common coordinate pixels in every two consecutive frame images in the specific analyzed frame images $I_1$ are calculated, and the maximum difference or ratio is extracted as a calculation signal value. The analyzed image acquired through this process can be viewed to readily determine the maximum value of the time dependent velocity or acceleration. For example, the frames corresponding to expiration should be determined to be specific analyzed frames, to readily evaluate the ease of expiration. This facilitates the detection of disease regions having varying movement and/or acceleration, such as regions of occlusive diseases and restrictive diseases.

In the process of determining the minimum derivative, the differences or ratio between the signal values of common coordinate pixels in every two consecutive frame images in the specific analyzed frame images $I_1$ are calculated, and the minimum difference or ratio is extracted as a calculation signal value. The analyzed image acquired through this process can be viewed to readily determine the minimum value of the time dependent velocity or acceleration. For example, the frames corresponding to expiration should be determined to be specific analyzed frames, to readily evaluate the ease of expiration. This facilitates the detection of disease regions having varying movement and/or acceleration, such as regions of occlusive diseases and restrictive diseases.

In response to an instruction for subjecting different analyzed moving images to concurrent calculation (by dragging and dropping the moving images to a summary display region 15A), the controller 11 subjects each of the analyzed moving image to calculation.

The controller 11 causes the calculated images $I_2$ based on the calculation image data generated through the calculation processes to appear on the display 15 in response to an automatic instruction or a user instruction. In other words, the controller 11 functions as an image display means according to the present invention.

The radiation image processing apparatus 1 according to this embodiment defines a summary display region 15A in at least a portion of the display region of the display 15. The summary display region 15A is a region mainly for display of the calculated images $I_2$.

The summary display region 15A may be constantly displayed or may be switched between displayed or not displayed as required. The summary display region 15A may appear on a portion of the display 15 or the entire display 15.

Alternatively, the summary display region 15A may appear on a display other than the display 15.

The summary display region 15A displays the calculated images $I_2$ and other images in various modes. In this embodiment, images can be displayed in the summary display region 15A in four display modes: a single image mode, a parallel mode, a superposition mode, and a switching mode.

The calculated images $I_2$ may be displayed not only in the summary display region 15A but also in the display 15.

In the single image mode, one summary display region 15A displays one calculated image $I_2$, as illustrated in FIG. 2, for example.

Several summary display regions 15A in the single image mode may be simultaneously displayed.

Figure 4C:
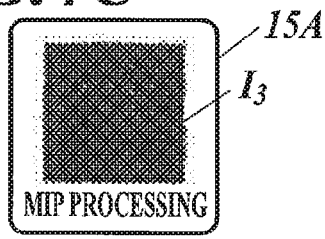
Figure 5:
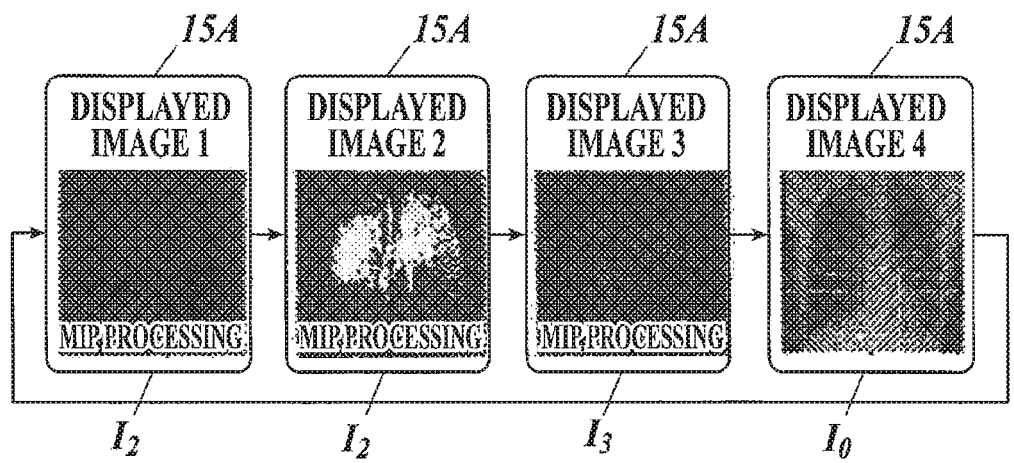
FIG. 5 illustrates example results of the image processing displayed by the radiation image processing apparatus according to the first embodiment.

In the superposition mode, a calculated image $I_2$ is superposed on an original moving image $I_0$, an original frame image $I_0$, an analyzed moving image $I_1$, an analyzed frame image $I_1$, and/or another calculated image $I_2$, as illustrated in FIGS. 2 and 4C. It should be noted that FIG. 2 illustrates a calculated image $I_2$ superposed on the original moving image or original frame image $I_0$. FIG. 4C illustrates a calculated image $I_2$ superposed on another calculated image $I_2$, where the two calculated images $I_2$ are obtained by subjecting two image data items subjected to different analytical processes to the same calculation process (MIP process).

Alternatively, three or more images may be superposed.

Hereinafter, an image displayed in the superposition mode is referred to as superposed image $I_3$.

Figure 4D:
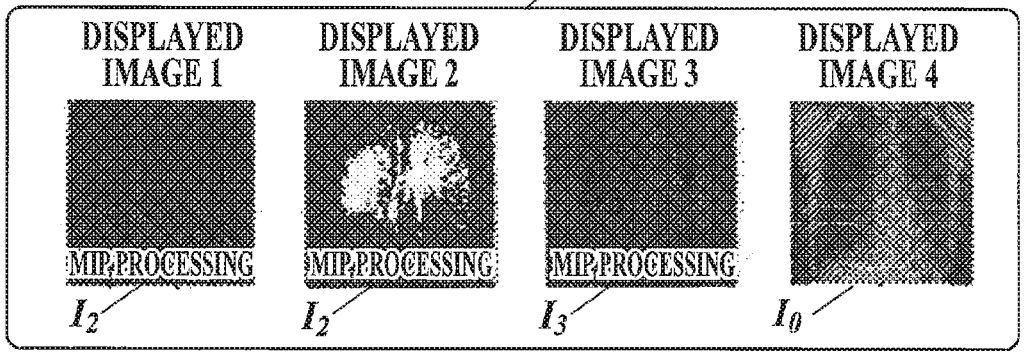

In the parallel mode, a calculated image $I_2$ is displayed in parallel with an original moving image $I_0$, an original frame image $I_0$, an analyzed moving image $I_1$, an analyzed frame image $I_1$, another calculated image $I_2$, and/or a superposed image $I_3$, as illustrated in FIGS. 3, 4B, and 4D. It should be noted that FIG. 3 illustrates an array of calculated images $I_2$ obtained by subjecting different numbers of specific analyzed frame images $I_1$ to the same calculation process (MIP process); FIG. 4B illustrates two calculated images $I_2$ obtained by subjecting two image data items subjected to different analytical processes to the same calculation process (MIP process); and FIG. 4D illustrates an array of different calculated images $I_2$, a superposed image $I_3$ of the calculated images $I_2$, the original moving image or original frame image $I_0$.

As described above, the results of different calculation processes can be displayed in the parallel mode.

In the switching mode, one of a calculated image $I_2$, an original moving image $I_0$, an original frame image $I_0$, an analyzed moving image $I_1$, an analyzed frame image $I_1$, a calculated image $I_2$, and a superposed image $I_3$ is displayed for a predetermined time and switched to a different image, as illustrated in FIG. 5. It should be noted that FIG. 5 illustrates the switching of a calculated image $I_2$, another calculated image $I_2$, a superposed image $I_3$ of the calculated images $I_2$, and an original moving image or original frame image $I_0$, in this order.

The parallel mode may be combined with the switching mode. In specific, several images may be displayed in a single summary display region 15A while being switched.

In the display modes described above, the at least one image displayed in the summary display region 15A always includes a calculated image $I_2$. Alternatively, the at least one image displayed in the summary display region 15A may include no calculated image $I_2$. In specific, the original moving image or original frame images $I_0$, the analyzed moving image or analyzed frame images $I_1$ may be displayed in the superposition mode, the parallel mode, and the switching mode.

As described above, the radiation image processing apparatus 1 according to this embodiment includes an image acquisition means for acquiring moving image data of an original moving image (radiographic moving image) consisting of a plurality of original frame images; an analysis means for subjecting the moving image data acquired by the image acquisition means to a predetermined analytical process, to generate an analyzed moving image consisting of a plurality of analyzed frame images; a selection means for selecting a plurality of specific analyzed frame images from the plurality of analyzed frame images of the analyzed moving image generated by the analysis means; a calculation means for deriving a calculation signal value on the basis of signal values of a group of pixels having common coordinates (common coordinate pixels) in the specific analyzed frame images selected by the selection means; and an image display means for causing a calculated image based on the calculation signal values generated for all groups of pixels having common coordinates by the calculation means, to appear on a display.

The display of moving images or still images in the summary display regions 15A, as described above, allows the user to intuitively select the calculated images $I_2$ of high interest. As a result, the user can readily determine a display scheme suitable for diagnosis. This enhances the accuracy of interpretation of the images.

This also allows the user to readily focus on the relevant moving images appearing on the display 15 and efficiently interpret the images while preventing misinterpretation. As a result, the accuracy of the diagnosis is enhanced.

Any of the frame images can be selected. Thus, the frame images that are presumed to contain artifacts or noise can be readily removed. This enhances the accuracy of the analytical results.

In specific, the target information in the moving image can be readily interpreted. This reduces the burden on the user.

An array of calculated images $I_2$ obtained by subjecting different numbers of frame images to the same calculation process (MIP process) can be displayed in the parallel mode, as illustrated in FIG. 3, to promote intuitive and prompt determination of the adequacy of the calculation, i.e., whether the range of selected frames should be narrowed or widened, by the user.

The results of the calculation carried out on the frame images selected from different types of moving images (lists of frame images) can be displayed in the parallel mode, or the results of the calculation carried out on the frame images selected from the moving image can be superposed to each other, as illustrated in FIGS. 4B, 4C, and 4D. In this way, the user can readily prepare a "ventilation-perfusion (V/Q) image," which can be used in the diagnosis.

Second Embodiment

A radiation image processing apparatus according to a second embodiment of the present invention will now be described. FIGS. 6 to 9 are conceptual diagrams illustrating image selection by the radiation image processing apparatus according to this embodiment. FIG. 6 illustrates an example image of the lung field. The radiation image processing apparatus 1A according to this embodiment can process a moving image of any region besides the lung field that repeats the same movement in a predetermined cycle, such as the heart, the pulmonary artery, the main artery, or the pulmonary bronchus.

In the first embodiment, the user selects the specific analyzed frame images $I_1$ to be subjected to calculation. The radiation image processing apparatus 1A according to this embodiment automatically selects specific analyzed frame images $I_1$ on the basis of a predetermined selection pattern.

Thus, the execution control (the content of a memory 13A) of the radiation image processing apparatus 1A according to this embodiment differs from that according to the first embodiment. The configuration of the second embodiment is the same as that of the first embodiment, except for the content of the memory 13A.

In detail, the radiation image processing apparatus 1A stores several selection patterns for determining the range of automatic selection in the memory 13A and selects one of these predetermined selection patterns in accordance with a user operation of the operating unit 14. Selection of a region of interest (ROI) to be carefully interpreted (for example, the region indicated by reference sign R in FIG. 6A) by the user prompts automatic selection of the specific analyzed frame images in accordance with the selected selection pattern.

The radiation image processing apparatus 1A according to this embodiment has three main selection patterns: 1) local maximum (local minimum)—local maximum (local minimum); 2) local maximum (local minimum)—local minimum (local maximum); and 3) local maximum (local minimum) and the two predetermined areas immediately before and after the local maximum (local minimum).

Alternatively, one of these selection patterns may be preselected (selection by the user is not allowed) or the user may select one of two preselected patterns. Selection patterns other than those described above may further be provided.

Figure 6A:
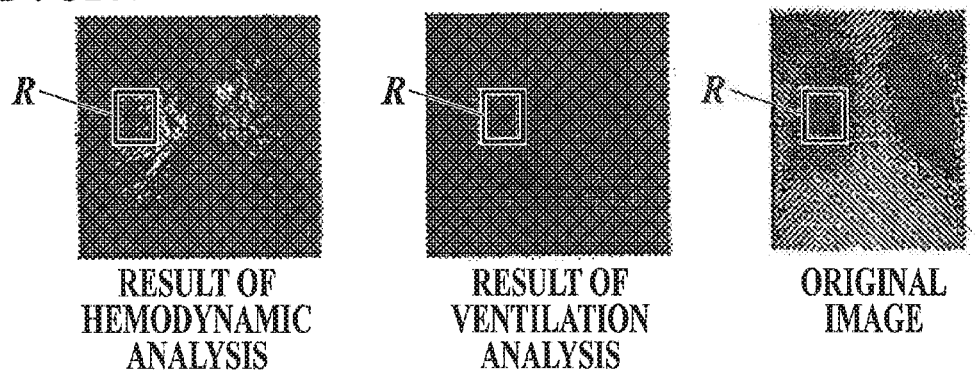
FIGS. 6A, 6B, and 6C are conceptual diagrams illustrating image selection by the radiation image processing apparatus according to the second embodiment.
Figure 6B:
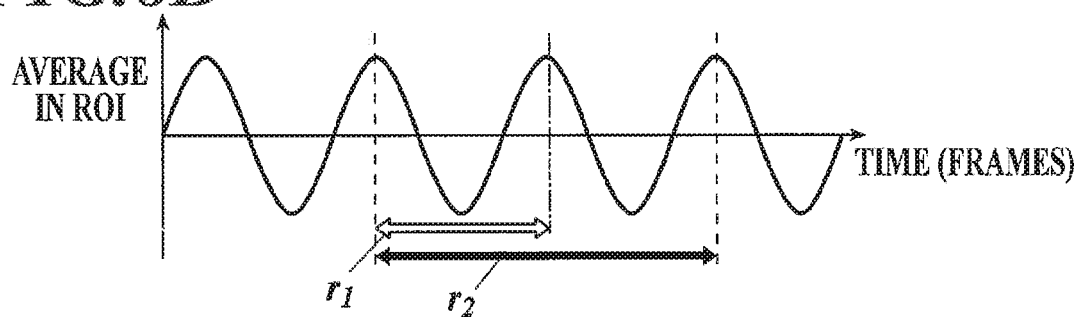
Figure 6C:
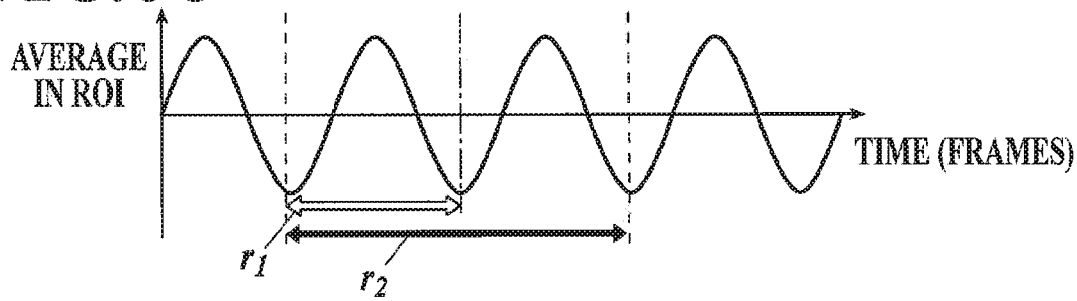

In response to the selection of the pattern (1), the radiation image processing apparatus 1A digitizes the temporal variation in the average pixel signal values in a region of interest (ROI) R containing at least a portion of the lung field, the heart, the pulmonary artery, the main artery, or the pulmonary bronchus (converted into a graph such as that illustrated in FIG. 6B). With reference to FIGS. 6B and 6C, frame images in a range $r_1$ from a local maximum (local minimum) to the adjacent local maximum (local minimum) (a moving image representing a movement of one cycle) or analyzed frame images in a range $r_2$ from a first local maximum (first local minimum) to a second local maximum (second local minimum) not adjacent to the first local maximum (first local minimum) (a moving image representing a movement of multiple cycles) are automatically selected as specific analyzed frame images.

One of the ranges $r_1$ and $r_2$ may be selected by the user when the user selects the selection pattern or may automatically be selected by the controller 11.

In the case where the diagnostic target is the lung field as illustrated in FIG. 6A, the selection range $r_1$ or $r_2$ represents a movement from an inspiratory level to the next inspiratory level. In the case where the diagnostic target is the heart, the selection range $r_1$ or $r_2$ represents a movement from systole to the next systole.

It is important that a movement corresponding to at least one cycle, for example, the movement of the lung during one breath or the movement of the heart during one heartbeat, should be interpreted to determine the pulmonary function. The selection pattern (1) of analyzed frame images enables accurate determination of the pulmonary function related to the aspiration cycle or the cardiac cycle (for example, the volume of air intake and output of the lung (ventilatory volume per cycle) or the blood intake or output of the lung field (cardiac output per cycle)).

In particular, a selection range $r_2$ corresponding to several cycles can reduce the variation in breathing and heartbeat.

In response to the selection of the selection pattern (2), the radiation image processing apparatus 1A digitizes the temporal variation in the averages in the ROI R (converted into a graph). Analyzed frame images in a selection range $r_3$ from a local maximum to the subsequent local minimum on the right in the graph, as illustrated in FIG. 7A, or analyzed frame images in a selection range $r_4$ from a local minimum to the subsequent local maximum on the right in the graph, as illustrated in FIG. 7B, are automatically selected as specific analyzed frame images.

Figure 7A:
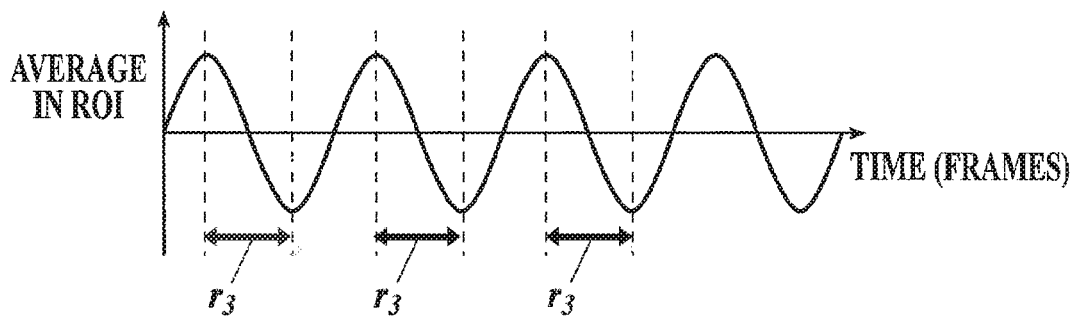
FIGS. 7A and 7B are conceptual diagrams illustrating the image selection by the radiation image processing apparatus according to the second embodiment.
Figure 7B:
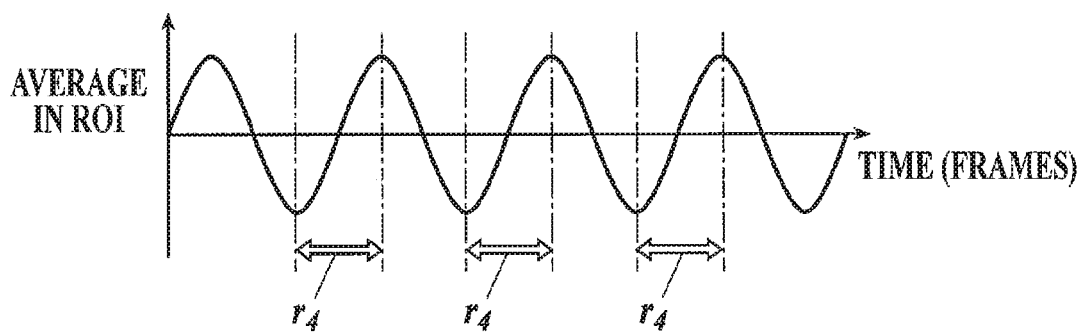

With reference to FIGS. 7A and 7B, the selection range $r_3$ or $r_4$ corresponding to several cycles may be defined in a single graph.

One of the ranges $r_3$ and $r_4$ should be selected by the user after the user selects the selection pattern of analyzed frame images or automatically selected by the controller 11.

In the case where the diagnostic target is the lung field, the selected range $r_3$ represents an expiratory movement and the selected range $r_4$ represents an inspiratory movement. In the case where the diagnostic target is the heart, the selected range $r_3$ or $r_4$ represents the systolic movement or the diastolic movement.

The analyzed frame images corresponding to multiple cycles of expiration (inspiration) or diastole (systole) can be subjected to calculation to reduce the influence of noise, such as a variation in breathing and heartbeat. This allows accurate observation of the systolic blood flow spreading through the lung field, the diastolic blood flow returning to the heart, the inspiratory expansion of the lung, and the expiratory contraction of the lung.

For example, this is useful in evaluation of difficulty of expiration in patients having occlusive diseases, difficulty of inspiration in patients having restrictive diseases or obese patients, and arrhythmia or irregular heart rhythm.

Figure 8A:
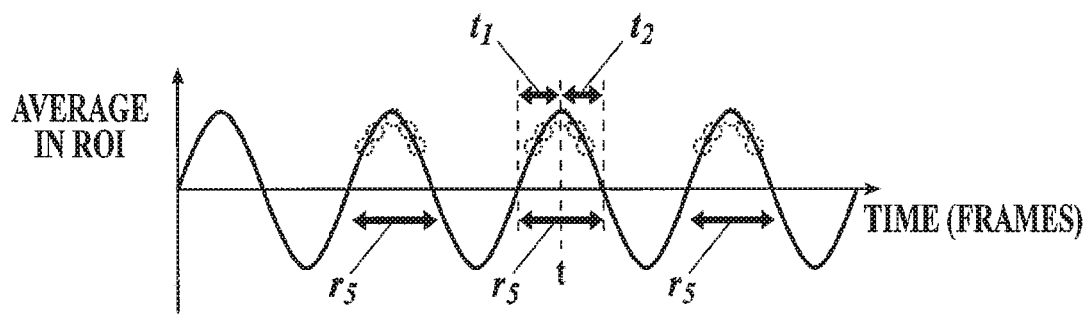
FIGS. 8A and 8B are conceptual diagrams illustrating the image selection by the radiation image processing apparatus according to the second embodiment.
Figure 8B:
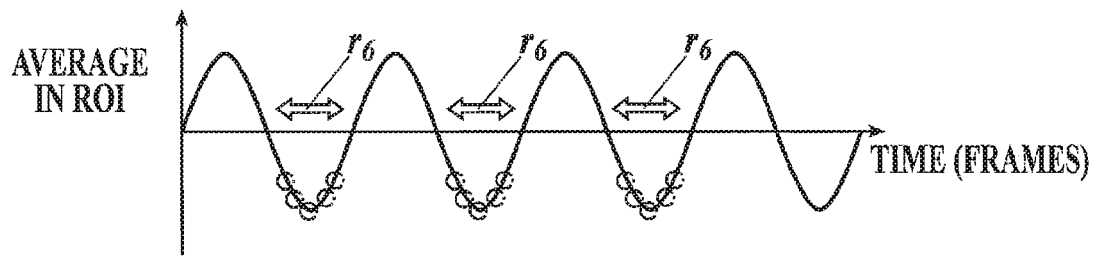

In response to the selection of the selection pattern (3), the radiation image processing apparatus 1A digitizes the temporal variation in the averages in the ROI R (converted into a graph). Analyzed frame images in a selection range $r_5$ from an analyzed frame image captured at a predetermined amount of time $t_1$ before a time t corresponding to a maximum local to an analyzed frame image captured at a predetermined amount of time $t_2$ after the time t ($t-t_1$ to $t+t_2$), as illustrated in FIG. 8A, or analyzed frame images in a selection range $r_6$ from an analyzed frame image captured at a predetermined amount of time $t_1$ before a time t corresponding to a minimum local to an analyzed frame image captured at a predetermined amount of time $t_2$ after the time t ($t-t_1$ to $t+t_2$), as illustrated in FIG. 8B, are automatically selected as specific analyzed frame images. The predetermined time periods $t_1$ and $t_2$ are each preferably at most ¼, more preferably, at most ⅛ a single aspiration or cardiac cycle.

In FIGS. 8A and 8B, the predetermined time periods $t_1$ and $t_2$ have the same length. Alternatively, the predetermined time periods $t_1$ and $t_2$ may have different lengths.

The selection range may be defined by the number of analyzed frame images from the local maximum, not by the time.

With reference to FIGS. 8A and 8B, the selection range $r_5$ or $r_6$ corresponding to several cycles may be defined in a single graph.

The aspiration or cardiac cycle of each patient may be measured with a spirometer, a MostGraph, or an electrocardiogram, or the average determined on the basis of nationality, height, sex, and/or age may be used.

In the case where the diagnostic target is the lung field, the local maximum and the vicinity thereof represent the movement near and at the inspiratory level, and the local minimum and the vicinity thereof represent the movement near and at the expiratory level. In the case where the diagnostic target is the heart, the local maximum and the vicinity thereof represent the movement near and at systole, and the local minimum and the vicinity thereof represent the movement near and at diastole.

The analyzed frame images corresponding to the expiratory level (inspiratory level) or diastole (systole) can be subjected to calculation to accurately observe the systolic blood flow fully spreading through the lung field, the diastolic blood flow fully returning to the heart, the full inspiratory expansion of the lung, and the full expiratory contraction of the lung.

The blood flowing from the heart to the lungs has a high flow rate. This prevents ready determination of the flow path of the blood in the lung field merely on the basis of usual analytical results or a moving image. It is disadvantageous to subject all analyzed frame images to calculation because many artifacts are included. The analyzed frame images immediately before and after the full spread of blood through the lung field can be subjected to the calculation to obtain a pulmonary perfusion distribution image including fewer artifacts. In specific, the specific analyzed frame images selected on the basis of the selection pattern (3) are useful in determining a disease related to pulmonary perfusion. For example, they are useful in determining a region having a local absence of pulmonary perfusion, such as pulmonary embolism, or evaluation of cardiac arrest or cardiomegaly, which cause reduced cardiac functions. For the same reason described above, the specific analyzed frame images selected on the basis of the selection pattern (3) are ventilation function images including few artifacts. Thus, they are useful for evaluation of the expansion of the lungs, such as determination of a local absence of pulmonary ventilation and spreading of the diaphragm.

In response to the selection of the specific analyzed frame images of multiple cycles, the calculated images in each selection range may appear in the summary display region 15A in the parallel mode.

In this way, the most normal and abnormal breath or heartbeat can be readily determined.

Figure 9A:
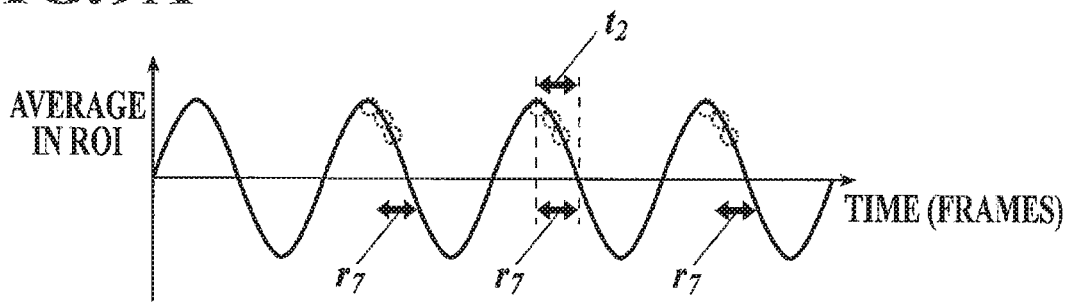
FIGS. 9A, 9B, 9C, and 9D are conceptual diagrams illustrating the image selection by the radiation image processing apparatus according to the second embodiment.
Figure 9B:
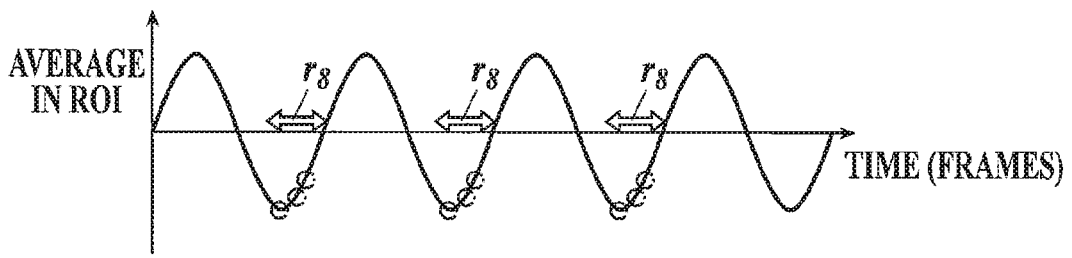
Figure 9C:
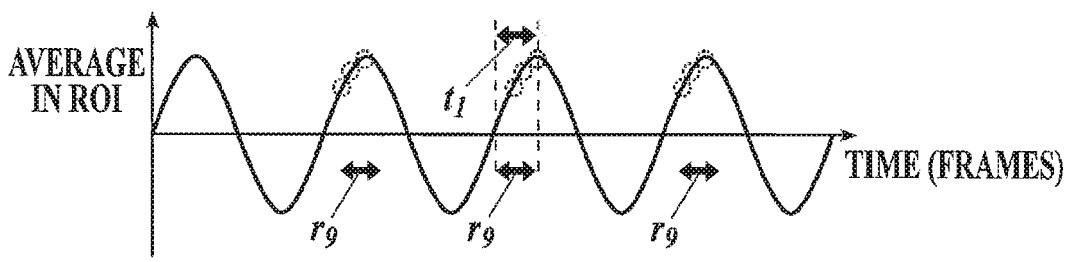
Figure 9D:
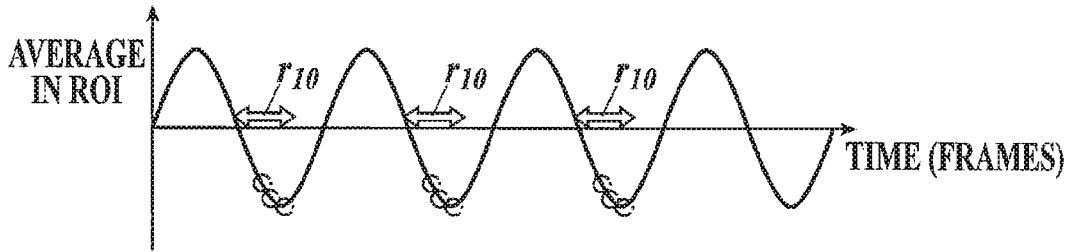

Alternatively, one of the predetermined time periods $t_1$ and $t_2$ in the selection pattern (3) may be zero. In detail, analyzed frame images captured in the following selection ranges may be automatically selected as specific analyzed frame images: a selection range $r_7$ from a time t corresponding to a local maximum to predetermined amount of time $t_2$ after the time t (local maximum to t+$t_2$), as illustrated in FIG. 9A; a selection range $r_8$ from a time t corresponding to a local minimum to a predetermined amount of time $t_2$ after the time t (local minimum to t+$t_2$), as illustrated in FIG. 9B; a selection range $r_9$ from a predetermined amount of time $t_1$ before a time t corresponding to a local maximum to the local maximum (t–$t_1$ to local maximum), as illustrated in FIG. 9C; and a selection range $r_{10}$ from a predetermined amount of time $t_1$ before a time t corresponding to a local minimum to the local minimum (t–$t_1$ to local minimum), as illustrated in FIG. 9D.

In this embodiment, the temporal variation in the average of the pixel signal values in the ROI R is digitized (converted into a graph), and then the specific analyzed frame images are selected. Alternatively, the specific analyzed frame images may be selected on the basis of other statistical values (for example, the maximum, the minimum, the mode, the integral, or the standard deviation).

Alternatively, the specific analyzed frame images may be selected on the basis of a temporal variation in morphological information, such as a temporal variation in the shift of the diaphragm, the area of the lung field, the variation in the distance between the ribs, the horizontal expansion of the lung field, the area of the heart, or the position of the aortic arch.

In the case of a target having, for example, an uneven distribution of fat and muscle in the lung field or the heart region (which is common in obese or female patients) or frequently moving in the vertical and horizontal directions (having large body motion) during image capturing, the breathing or cardiac state is not always accurately represented by the information on the temporal variation based on pixel values. The temporal variation in morphological information can be used to accurately select the specific analyzed frame images even for such patients.

Third Embodiment

Figure 10:
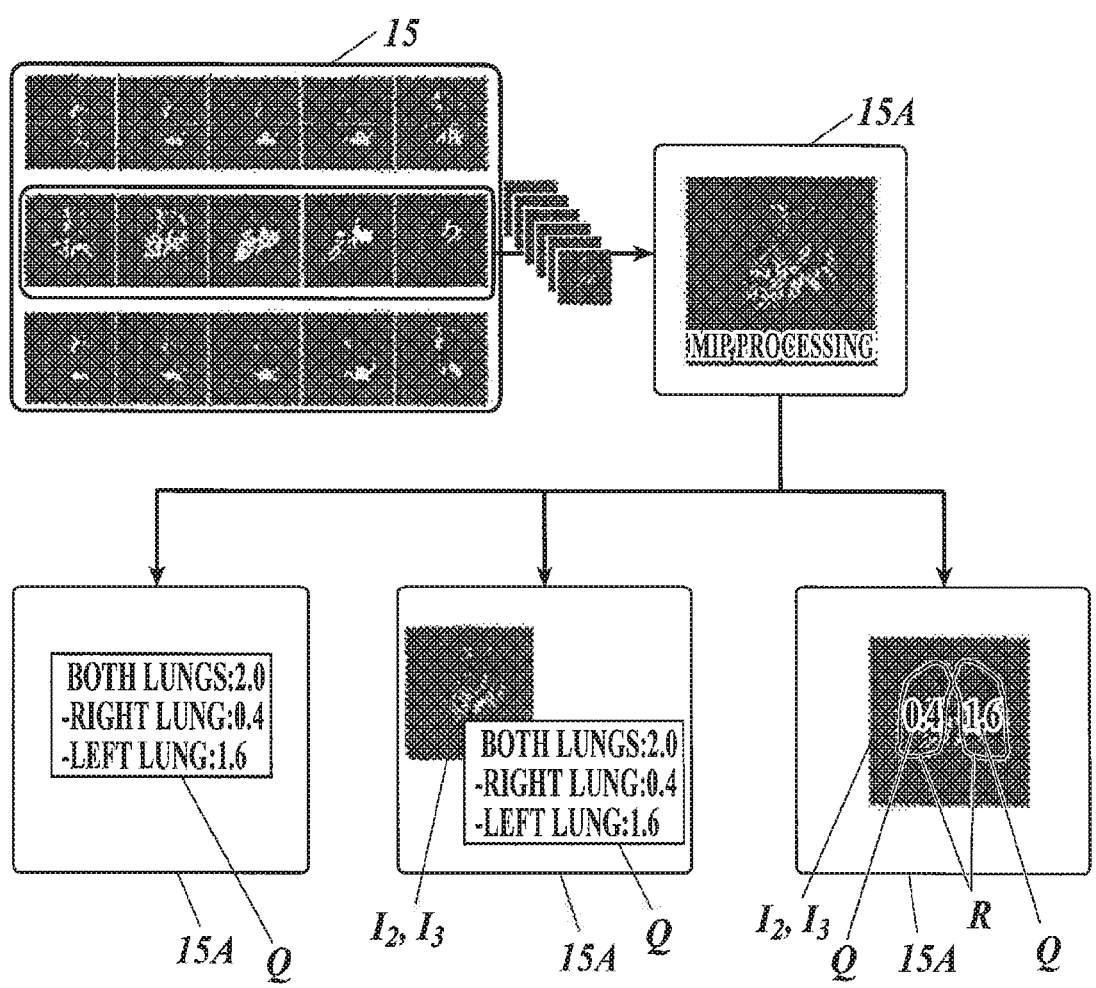
FIG. 10 is a conceptual diagram illustrating image selection by the radiation image processing apparatus according to the third embodiment of the present invention.
Figure 11:
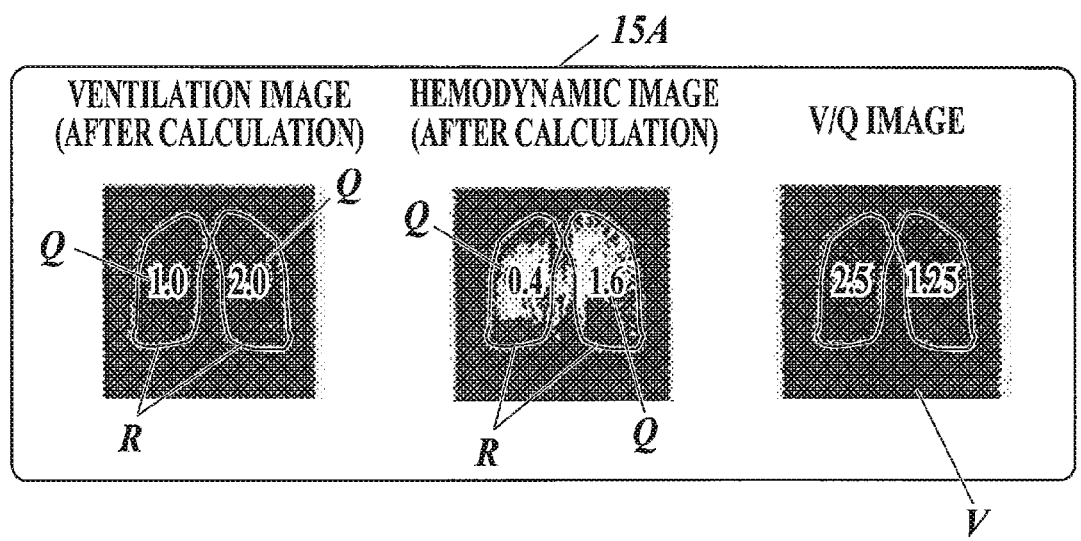
FIG. 11 illustrates example results of image processing displayed by the radiation image processing apparatus according to the third embodiment.

A radiation image processing apparatus 1B according to a third embodiment of the present invention will now be described. FIG. 10 is a conceptual diagram of image processing by the radiation image processing apparatus 1B. FIGS. 11 and 12 illustrate example display of the results of the image processing.

Although FIG. 10 illustrates an image of the lung field, the radiation image processing apparatus 1B according to this embodiment can process and display moving images capturing regions besides the lung field.

In the first and second embodiments, the summary display region 15A displays only images. The summary display region 15A of the radiation image processing apparatus 1B according to this embodiment displays predetermined quantitative values.

Thus, the execution control (the content of a memory 13B) of the radiation image processing apparatus 1B according to this embodiment differs from that according to the first and second embodiments. The configuration of the third embodiment is the same as that of the first and second embodiments, except for the content of the memory 13B.

The controller 11 of the radiation image processing apparatus 1B calculates multiple calculation signal values and derives a quantitative value Q on the basis of the signal values of multiple pixels in the ROI R of a calculated image. In other words, the controller 11 functions as a quantitative-value calculation means. The ROI R is a specific region according to the present invention. Hereinafter, the pixels residing in the ROI R are referred to as regional pixels. Several ROIs R may be defined. In such a case, a quantitative value Q may be determined for each ROI R, or the ROIs R may be collectively treated as a single ROI and one quantitative value Q may be determined to the single ROI.

A quantitative value Q can be determined through a process of determining, for example, the maximum, the minimum, the Pk-Pk value, the standard deviation, the average, the mode, or the integral.

In the process of determining the maximum (minimum), a maximum (minimum) value is extracted from signal values of a plurality of regional pixels residing in the ROI R in a calculated image and determined as a quantitative value Q. The quantitative value Q determined through this process can be used for follow-up (deterioration or recovery of ventilation or blood flow) or comparison between left and right pulmonary functions. In particular, the maximum (minimum) feature value related to pulmonary ventilation, pulmonary perfusion, and cardiac functions can be determined at low computational costs. This is useful in, for example, monitoring before and after a treatment (monitoring of a variation in vital capacity and blood pressure).

In the process of determining the mode, the mode is extracted from the signal values of regional pixels and determined as a quantitative value Q. The quantitative value Q determined through this process can be used for follow-up or comparison between left and right pulmonary functions. In particular, the influence of artifacts, such as specific defects of pixels, in the calculated images can be reduced. This allows accurate determination of pulmonary ventilation, pulmonary perfusion, and cardiac functions in the ROI R.

In the process of determining the Pk-Pk value, the maximum and minimum values are extracted from the signal values of regional pixels, the difference between the maximum and minimum values is calculated, and the ratio of the difference between the maximum and minimum values to the number of regional pixels is calculated as a quantitative value Q. The quantitative value Q determined through this process can be used for follow-up or comparison between left and right pulmonary functions. In particular, the variation in feature values related to the pulmonary ventilation, pulmonary perfusion, and cardiac functions can be determined. In this way, the variation in the feature values of the respective functions in the ROI R (diseases that cause local abnormalities in the pulmonary ventilation and pulmonary perfusion functions) can be readily determined.

In the process determining the standard deviation, the standard deviation of the signal values of regional pixels is calculated as a quantitative value Q. The quantitative value Q determined through this process can be used for follow-up or comparison between left and right pulmonary functions. In particular, the variation in feature values related to the pulmonary ventilation, pulmonary perfusion, and cardiac functions can be determined at low computational costs. In this way, the variation in these functions in the ROIs R can be readily determined.

In the process determining the average, the average of the signal values of regional pixels is calculated as a quantitative value Q. The quantitative value Q determined through this process can be used for follow-up or comparison between left and right pulmonary functions. In particular, the pulmonary ventilation, pulmonary perfusion, and cardiac functions in the ROI R can be determined at low computational costs.

In the process determining the integral, the signal values of regional pixels are integrated into a quantitative value Q. The quantitative value Q determined through this process can be used for follow-up or comparison between left and right pulmonary functions. In particular, the quantitative value Q is determined with a small variation even when the ROI R is defined with a slight variation. This prevents or reduces measurement errors. The overall functions of the lung and the heart in the ROI R can be readily determined.

Alternatively, the quantitative value Q may be the number (area) of pixels among all pixels in the calculated image having signal values greater than or equal to or smaller than or equal to a predetermined threshold, or within a predetermined range, besides deriving the quantitative value Q on the basis of the signal values of the regional pixels in the ROI R.

In this way, for example, the percentage of a normal or abnormal lung region to the entire lung (total lung area) can be readily determined, and the local functional distribution of the lung (the location of a reduction or absence in pulmonary function) can be readily evaluated.

In this embodiment, the ROI R may be defined in the entire image region, the lung field, the heart region, the pulmonary artery, the main artery, and the pulmonary bronchus.

A quantitative value Q of a ROI R corresponding to the entire image region can be used to readily determine the pulmonary ventilation, pulmonary perfusion, and cardiac functions in a broad view without high computational costs.

A quantitative value Q of a ROI R corresponding to the lung field can be used to determine the pulmonary ventilation function (including a variation in the density in proportion to aspiration, and the movements of the diaphragm, the ribs, the clavicles, and the scapulae) and the pulmonary perfusion function (including a variation in the density in proportion to heartbeats and the movement of blood vessels).

A quantitative value Q of a ROI R corresponding to the heart region can be used to determine the cardiac function (shift of the cardiac wall (shift rate and/or acceleration) and a variation in the density in proportion to the heartbeat (rate of variation in density and acceleration of variation in density)).

A quantitative value Q of a ROI R corresponding to the pulmonary artery can be used to determine the pulmonary ventilation and pulmonary perfusion functions.

A quantitative value Q of a ROI R corresponding to the main artery can be used to determine the hemodynamic function in the systemic circulation (including a variation in the density in proportion to the heartbeat and the movement of the blood vessels) and the cardiac function.

A quantitative value Q of a ROI R corresponding to the pulmonary bronchus can be used to determine the pulmonary ventilation function, the degree of thickening of the respiratory tract, the degree of contraction of the respiratory tract, and the presence of atelectasis, pleural effusion, tumor mass, cyst, or emphysema.

The quantitative values Q may be displayed alone or together with images, as illustrated in FIG. 10.

As illustrated in FIG. 10, the images $I_2$ and $I_3$ can be displayed together with the quantitative values Q in the parallel mode, the switching mode, or the superposition mode.

Alternatively, the ROIs R of the images $I_2$ and $I_3$ can be displayed in the superposition mode, and the quantitative values Q may be displayed in the superposed image, as illustrated in FIG. 10. In this way, the pulmonary function of the left and right lungs can be intuitively determined.

In the case of frame images selected from each group of different types of frame images (by dragging and dropping the frame images to the summary display region 15A), the controller 11 generates calculated images $I_2$ of the moving images and calculates quantitative values Q for the moving images.

At this time, a quantitative value Q calculated for a ventilation analysis moving image (analyzed moving image) and a feature value (ratio or difference) based on a quantitative value Q calculated for a hemodynamic analysis moving image (analyzed moving image) may be displayed in the form of a V/Q image V representing the V/Q ratio (ratio of ventilation to blood flow), as illustrated in FIG. 11.

In this way, the user can readily determine the normality or abnormality of a region and also conduct a temporal comparison of the region.

Figure 12A:
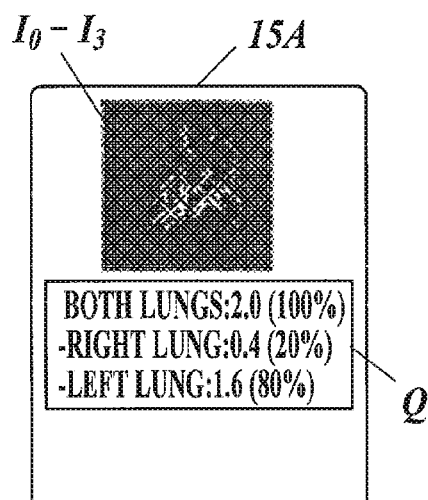
FIGS. 12A and 12B illustrate example results of the image processing displayed by the radiation image processing apparatus according to the third embodiment.

With reference to FIG. 12A, quantitative values Q for the left and right lungs may be calculated, and the ratios of the quantitative values Q of the left and right lungs may be displayed together with the quantitative values Q. In this way, the non-uniform functions of the left and right lungs can be readily determined, and thus the normality and abnormality can be readily determined.

Figure 12B:
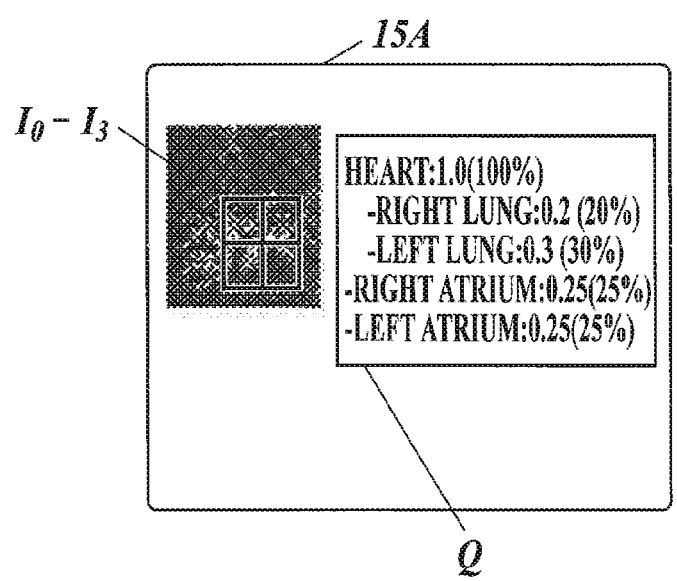

For diagnosis of the heart region, quantitative values Q and their ratios may be calculated and displayed for the ventricles, the atriums, the right side of the heart, and the left side of the heart, as illustrated in FIG. 12B. In this way, the non-uniform functions of the heart can be readily determined, and thus the normality and abnormality can be readily determined.

The quantitative values Q calculated in this embodiment can be stored in the headers of the calculated images $I_2$ when the images are stored. In this way, the header information can be confirmed in a list of file names of the calculated images $I_2$ when the calculated images $I_2$ are to be reloaded, and the quantitative values Q can be displayed only if necessary.

Alternatively, the quantitative values Q may be stored as data separate from the images (for example, text or CSV files). In this way, only the quantitative values Q can be readily reviewed without excessive opening of the image files. This enhances the efficiency of work, such as follow-up.

(First Modification)

In the embodiment described above, the calculated images and quantitative values Q based on the selected analyzed frame images are displayed in the summary display region 15A. Alternatively, several frame images selected by dragging and dropping them to the summary display region 15A may be simply displayed, as illustrated in FIG. 13.

In this modification, as in the embodiment described above, the frame images to be selected are not always consecutive frame images. The summary display region 15A may automatically display the frame images after selection or display the frame images in response to a user operation (for example, clicking of the OK button).

Figure 14A:
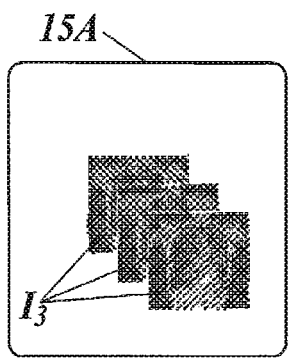
FIGS. 14A, 14B, and 14C illustrate example results of the image processing displayed by the radiation image processing apparatus according to the modification.
Figure 14B:
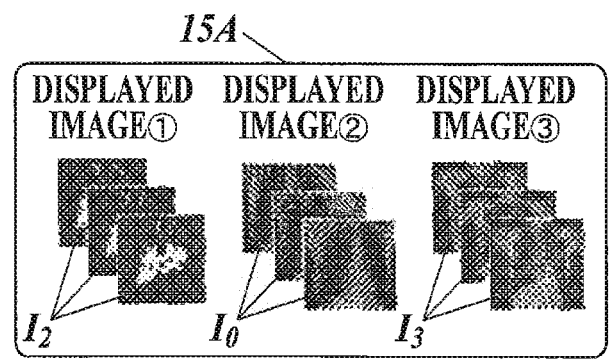
Figure 14C:
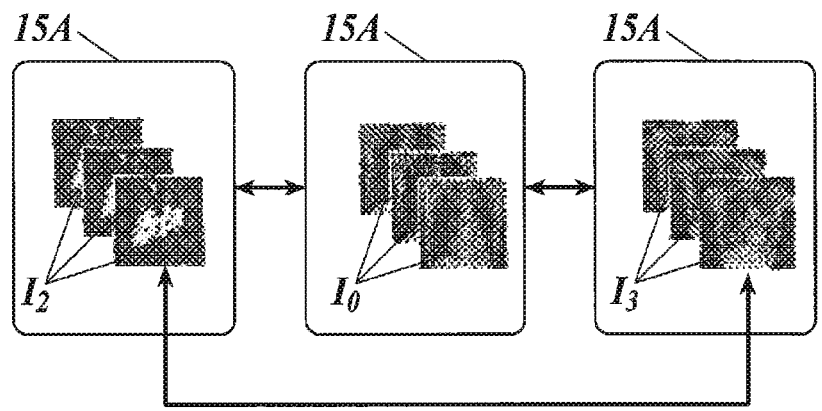

In the case where frame images are selected from lists of different types of frame images, the superposed image $I_3$ are displayed as illustrated in FIG. 14A (the original frame images and the analyzed frame images are displayed in the superposition mode in this modification), images are displayed in the parallel mode as illustrated in FIG. 14B (the calculated images $I_2$, the original frame images $I_0$, and the superposed image $I_3$ are displayed in the parallel mode in this modification), or images are displayed in the switching mode as illustrated in FIG. 14C (the calculated images $I_2$, the original frame images $I_0$, and the superposed image $I_3$ are displayed in the switching mode in this modification).

The same or different number of frame images may be selected from the groups of different types of moving images.

According to this modification, only frame images of high interest of the user are displayed in the summary display region 15A. This allows the user to readily focus on interpretation of the images, and thus enhances the accuracy of the interpretation.

In particular, displaying only frame images corresponding to an integral multiple of the aspiration cycle, for example, one breath, in the summary display region 15A facilitates evaluation of normal aspiration.

Displaying only frame images corresponding to an integral multiple of the heart cycle, for example, one heartbeat, in the summary display region 15A facilitates evaluation of normal heart movement.

Displaying only frame images corresponding to the beginning of inspiration or expiration in the summary display region 15A facilitates evaluation of difficulty in inspiration or expiration in patients having respiratory disorders.

Displaying only frame images corresponding to systole or diastole in the summary display region 15A facilitates evaluation of blood intake, blood output, arrhythmia, and cardiomegaly in patients having cardiac disorders.

The group of frame images used to determine the normality or abnormality of the pulmonary function is displayed in the summary display region 15A and compared to the list of frame images preliminarily displayed on the display 15. In this way, the frame images preliminarily displayed on the display 15 can be readily and comprehensively determined to be normal or abnormal. In specific, this enhances the efficiency of interpretation of the frame images preliminarily displayed on the display.

With reference to FIG. 15, the results of a ventilation analysis are superposed to the results of a hemodynamic analysis and displayed in the summary display region 15A, to readily obtain an image equivalent to an image comparing the ventilation and hemodynamic functions (V/Q image).

This enables comparison of the ventilation and hemodynamic functions with only the frame images selected by the user. Thus, a V/Q image under low influence of artifacts can be obtained, and the accuracy of diagnosis is enhanced.

With reference to FIG. 15, the results of the ventilation analysis and the hemodynamic analysis, and superposed images and the original images of these results may be displayed in the parallel or switching mode.

(Second Modification)

Figure 16:
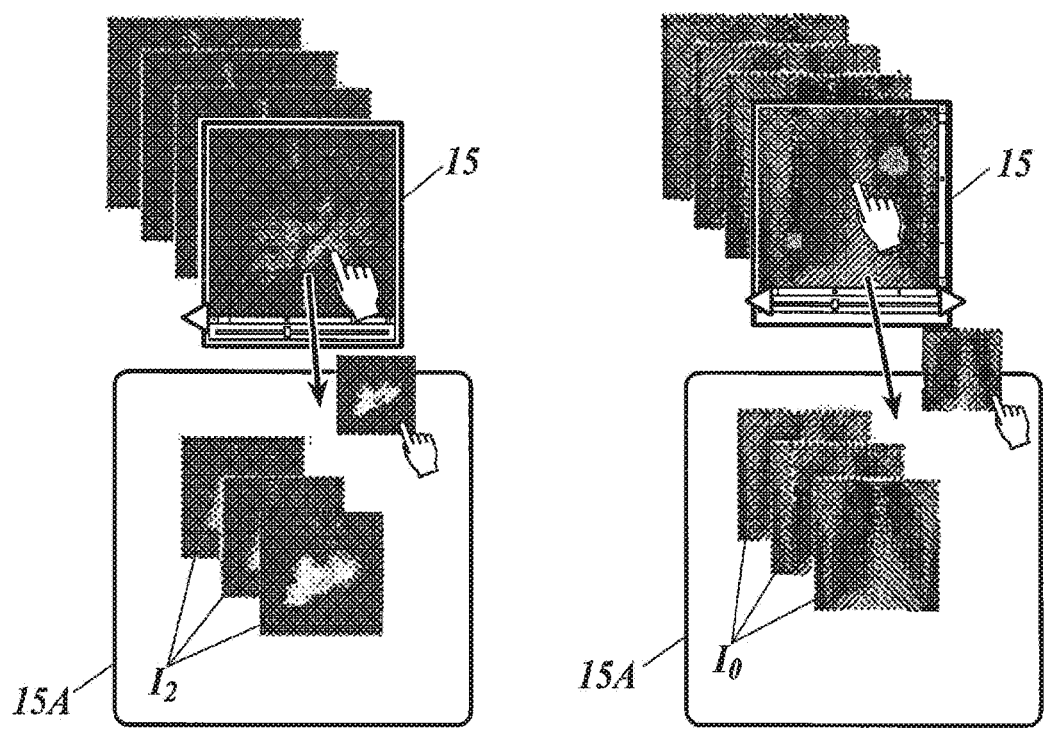
FIG. 16 is a conceptual diagram illustrating the image processing by the radiation image processing apparatus according to the modification.

In the embodiment described above, frame images for the display of analyzed moving image in the summary display region 15A are selected from a list of frame images displayed on the display 15. Alternatively, the moving image may be played back on the display 15, and the necessary images may be directly dragged and dropped from the moving image to the summary display region 15A, as illustrated in FIG. 16.

With reference to FIG. 17, checkboxes B may be disposed on the frame images, and the frame images corresponding to the checkboxes B having checks C may be displayed in the summary display region 15A. In this way, the user can select the frame images by placing the checks C in the checkboxes B while viewing the frame images or moving image displayed in the summary display region 15A. Thus, the user can promptly determine whether the selected frame images are appropriate for diagnosis.

(Third Modification)

Figure 18:
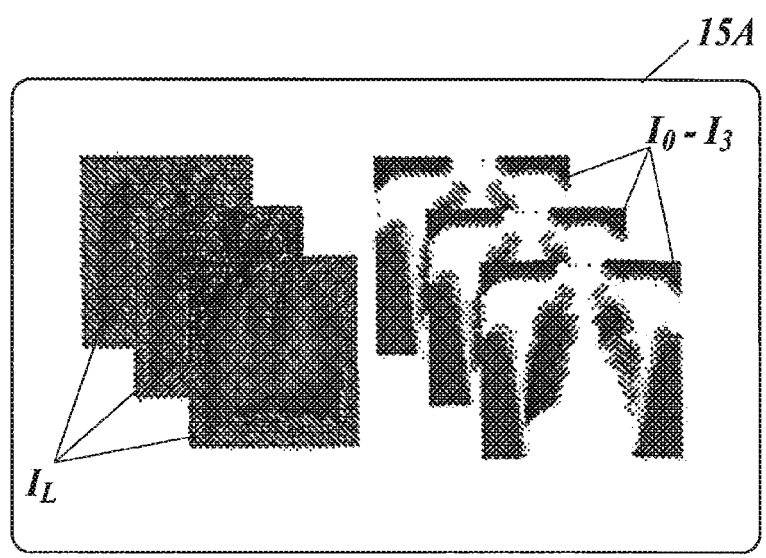
FIG. 18 illustrates example results of the image processing displayed by the radiation image processing apparatus according to the modification.

With reference to FIG. 18, the selected frame images displayed in the summary display region 15A may be images $I_L$ with reference to a lookup table (LUT) different from those of the unselected frame images and moving images. In detail, the density, contrast, and color map are modified before display.

In this way, images of high interest of the user are emphasized with colors that attract the attention of the user before displayed in the summary display region 15A. Thus, the user can readily focus on the interpretation and enhance accuracy of the interpretation.

Although embodiments of the present invention have been described and illustrated in detail, the disclosed embodiments are made for purposes of illustration and example only and not limitation. The scope of the present invention should be interpreted by terms of the appended claims

What is claimed is:
1. A radiation image processing apparatus comprising:
a display which displays an image; and
a hardware processor which is configured to,
  acquire radiographic moving image data comprising a plurality of frame images,
  subject the moving image data to predetermined analytical processing,
  generate an analyzed moving image comprising a plurality of analyzed frame images,
  select a plurality of specific analyzed frame images from the analyzed frame images of the analyzed moving image,
  derive a calculation signal value based on signal values of pixels having common coordinates positioned in common coordinates in the selected specific analyzed frame images, and
  cause a calculated image based on the calculation signal values generated for each of the coordinates to appear on the display,
wherein the hardware processor
extracts a maximum, a minimum, or a mode of the signal values of pixels having common coordinates in the specific analyzed frame images, and
calculates a ratio of a difference between the maximum and the minimum of the signal values of the pixels having common coordinates to the number of selected specific analyzed frame images, calculates a standard deviation of the signal values of the pixels having common coordinates, or calculates an integral of the signal values of the pixels having common coordinates, or calculates differences between the signal values of pixels having common coordinates in every two consecutive specific analyzed frame images and derives the calculation signal value through extraction of a maximum or a minimum of the differences.

2. The radiation image processing apparatus according to claim 1, wherein the hardware processor defines a summary display region in at least a portion of the display region of the display and causes the calculated images to appear in the summary display region.

3. The radiation image processing apparatus according to claim 1, further comprising:

an operating unit operated by a user, wherein the hardware processor selects the specific analyzed frame images based on a user operation of the operating unit.

4. The radiation image processing apparatus according to claim 1, wherein the hardware processor automatically selects the specific analyzed frame images based on a predetermined selection pattern.

5. The radiation image processing apparatus according to claim 4, further comprising:

an operating unit operated by a user, wherein the hardware processor sets a selection pattern from a plurality of preliminarily prepared selection patterns based on a user operation of the operating unit, and the hardware processor automatically selects the specific analyzed frame images based on the set selection pattern.

6. The radiation image processing apparatus according to claim 1, wherein the hardware processor calculates the calculation signal values and derives a predetermined quantitative value based on signal values of regional pixels residing in a specific region in the calculated image, and causes the calculated quantitative value to appear in the summary display region.

7. The radiation image processing apparatus according to claim 6, wherein the hardware processor, extracts a maximum, a minimum, or a mode from the signal values of the regional pixels, or derives the quantitative value through calculation of a ratio of a difference between the maximum and the minimum of the signal values of the regional pixels to the number of regional pixels, or a standard deviation, an average, or an integral of the signal values of the regional pixels.

8. The radiation image processing apparatus according to claim 7, wherein the specific region is defined in a lung field, a heart region, a pulmonary artery, a main artery, or a pulmonary bronchus.

9. A radiation image capturing system comprising:

a radiation irradiator emitting radiation;

a radiographic-image capturing apparatus receiving radiation from the radiation irradiator and generating radiographic image data; and the radiation image processing apparatus according to claim 1 directly or indirectly connected to the radiographic-image capturing apparatus to establish communication between the radiographic-image capturing apparatus and the radiation image processing apparatus, wherein emission of radiation from the radiation irradiator and reading of the image data by the radiographic-image capturing apparatus are continuously repeated to generate radiographic moving image data.

* * * * *